United States Patent [19]

Nishizawa et al.

[11] 4,429,163
[45] Jan. 31, 1984

[54] PREPARATION OF P-HYDROXYBENZALDEHYDE DERIVATIVES

[75] Inventors: Kanji Nishizawa, Takatsuki; Kazuhiko Hamada; Tadatoshi Aratani, both of Ibaraki, all of Japan

[73] Assignee: Sumitomo Chemical Company, Limited, Osaka, Japan

[21] Appl. No.: 289,991

[22] Filed: Aug. 4, 1981

Related U.S. Application Data

[63] Continuation of Ser. No. 99,714, Dec. 3, 1979, abandoned.

[30] Foreign Application Priority Data

Dec. 13, 1978 [JP] Japan .............................. 53-155974

[51] Int. Cl.³ ............................................. C07C 45/36
[52] U.S. Cl. ................................... 568/432; 568/626
[58] Field of Search .................................. 568/432

[56] References Cited

U.S. PATENT DOCUMENTS

| | | | |
|---|---|---|---|
| 3,164,611 | 1/1965 | Sarett | 568/432 |
| 3,321,526 | 5/1967 | Marchand et al. | 568/432 |
| 3,931,330 | 1/1976 | Aprahamian | 568/432 |
| 4,113,782 | 9/1978 | Juichi et al. | 568/432 |

FOREIGN PATENT DOCUMENTS

2605678 9/1976 Fed. Rep. of Germany ...... 568/432

OTHER PUBLICATIONS

Nishinaga et al., Angew. Chem., Int, Edit, vol. 14 (1975) p. 3565.

Nishinaga et al., J.A.C.S., vol. 100, pp. 1820–1825, (1978).

Primary Examiner—James H. Reamer
Attorney, Agent, or Firm—Stevens, Davis, Miller & Mosher

[57] ABSTRACT

A 4-hydroxybenzaldehyde derivative of the formula:

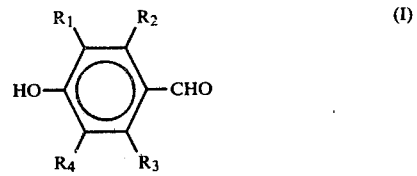

wherein each of $R_1$, $R_2$, $R_3$ and $R_4$ is selected from the group consisting of hydrogen atom, halogen atoms, lower alkyl groups or lower alkoxy groups, which is useful as intermediate for the production of medicines or agricultural chemicals, or as flavor, is produced by the reaction of a p-cresol derivative of the formula:

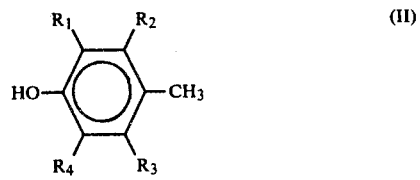

wherein each of $R_1$, $R_2$, $R_3$ and $R_4$ is as defined above, with oxygen or oxygen-containing gas in the presence of a base and a catalytic amount of cobalt compound or metallic cobalt.

9 Claims, No Drawings

PREPARATION OF P-HYDROXYBENZALDEHYDE DERIVATIVES

This is a continuation of application Ser. No. 99,714 filed on Dec. 3, 1979, now abandoned.

This invention relates to a process for preparing 4-hydroxybenzaldehyde derivatives by oxidizing a p-cresol derivative with oxygen in the presence of a base and a cobalt compound or metallic cobalt.

The 4-hydroxybenzaldehyde derivatives are not only an important material in the organic chemical industries but are also themselves very useful compounds which command a wide variety of uses including use as flavoring materials in particular. For example, 4-hydroxybenzaldehyde, and 3,5-di-tert-butyl-4-hydroxybenzaldehyde are important as an intermediate for the preparation of medicines or agricultural chemicals, while 3-alkoxy-4-hydroxybenzaldehyde is useful as a vanillin flavor.

There are known several methods for obtaining 4-hydroxybenzaldehyde derivatives, and one of such methods comprises oxidizing a corresponding p-cresol derivative with oxygen. This reaction may become an advantageous method in industrial applications, if selective oxidation into 4-hydroxybenzaldehyde can be attained in a high yield by using a suitable catalyst. This oxidation reaction, however, involves the following problems. Firstly, oxidation of the benzene nucleus may be liable to take precedence over that of the methyl group in the p-cresol derivative involved. Particularly, in the case of a p-cresol derivative having no substituent at the ortho-position of the hydroxyl group, it is known that the outcome of coupling at the ortho-position becomes the principal product (see for example R. F. Moore and W. A. Waters: J. Chem. Soc., 1954, 243). It is also known that, in oxidation of an aromatic compound having a methyl group, such as for example toluene, xylene, etc., a corresponding carboxylic acid is produced through formation of an aldehyde. Thus, generally, the oxidation rate of an aldehyde group is far higher than that of a methyl group, and it is difficult to obtain an aromatic aldehyde in a high yield by an oxygenation method.

For these reasons, there are presently availble only the following two methods for the selective preparation of a 4-hydroxybenzaldehyde derivative through oxygenation of a corresponding p-cresol derivative.

(1) An oxygenation method using potassium tertiary butoxide in excess in dimethylformamide [A. Nishinaga, T. Itahara and T. Matsuura: Angew. Chem., internat. Edit. 14 (1975), 356].

This method requires use of a specific solvent and base in great quantities, and also use of other starting materials than 2,6-di-substituted p-cresol, and results in a very poor yield.

(2) An oxygenation method using an N,N'-ethylenebis(salicylidene iminate)cobalt (II) catalyst in an alcohol solvent or using a cuprous chloride catalyst in a pyridine solvent (T. Shimizu, A. Nishinaga and T. Matsuura: A Collection of Abstracts of the Lectures at 12th Oxidation Reaction Forum, P. 74, 1978, Tokyo).

This method also specifies 2,6-di-substituted p-cresol as the starting material and requires use of a specific solvent and a large amount of catalyst, making its industrial application impractical.

In order to overcome these problems, the present inventors have made further researches into the method for selective and high-yield preparation of 4-hydroxybenzaldehyde derivatives by oxygenation of p-cresol derivatives in a wider range including the 2,6-unsubstituted p-cresol derivatives and finally reached the present invention.

Thus, the present invention provides a process for the production of 4-hydroxybenzaldehyde derivatives of the formula:

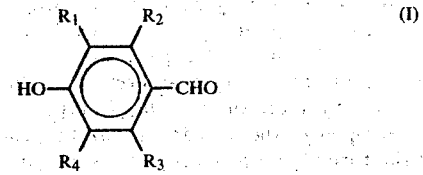

wherein each of $R_1$, $R_2$, $R_3$ and $R_4$ is selected from the group consisting of hydrogen atom, halogen atoms, lower alkyl groups and lower alkoxy groups which comprises the reaction of a p-cresol derivative of the formula:

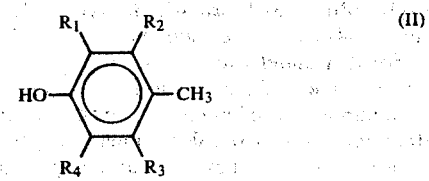

wherein each of $R_1$, $R_2$, $R_3$ and $R_4$ is as defined above with oxygen or oxygen-containing gas in a solvent in the presence of a base and a catalytic amount of a cobalt compound or metallic cobalt.

The process of this invention has the following salient features and advantages:

(1) The starting material used in this invention is open to a wider choice. It is possible according to the process of this invention to oxidize even the p-cresol derivatives having no substituent at the ortho-position of the hydroxyl group, for example p-cresol itself.

(2) The yield of the produced 4-hydroxybenzaldehyde derivative is higher than that obtainable from the aforementioned two conventional methods.

(3) Only the methyl group at the para-position of the hydroxyl group is selectively oxidized into a corresponding formyl group while the other substituents $R_1$, $R_2$, $R_3$ and $R_4$ remain unchanged.

(4) Mixed cresol derivatives can be conveniently used as the starting compound (II). For example, the process of the present invention can be carried out using a mixture of m- and p-cresols to obtain 4-hydroxybenzaldehyde as well as m-cresol recovered.

(5) A wide variety of cobalt compounds can be used as the catalyst, and no specific compound is required. Also, the amount of such cobalt compound used is minimized.

(6) Selection of the solvent is not subject to any specific restrictions, and a wider range of choice is possible.

The invention is now described in further detail.

As for the substituents $R_1$, $R_2$, $R_3$ and $R_4$ in the p-cresol derivatives of the formula (II) used as starting material in this invention, the halogen atom may be fluorine, chlorine, bromine or iodine, but chlorine and bromine are preferred. The lower alkyl groups usable in this invention have 1 to 6, preferably 1 to 4, carbon atoms, and include methyl group, ethyl group, propyl group, isopropyl group, n-butyl group, secondary butyl group, isobutyl group, tertiary butyl group, cyclohexyl group and the like. The lower alkoxy groups usable in this invention have 1 to 6, preferably 1 to 4, carbon atoms and include methoxy group, ethoxy group, propoxy group, isopropoxy group, n-butoxy group, secondary butoxy group, isobutoxy group, tertiary butoxy group, cyclohexyloxy group and the like. More definite examples of the p-cresol derivatives of the general formula (II) include p-cresol, 2,6-dichloro-p-cresol, 2-bromo-p-cresol, mesitol, 2,4-xylenol, 3,4-xylenol, 2,6-di-tert-butyl-p-cresol, 2-methoxy-p-cresol, 2,6-dimethoxy-p-cresol, 2-ethoxy-p-cresol, 2-chloro-p-cresol, 2,6-dibromo-p-cresol and 2-tert-butyl-p-cresol.

Examples of the p-hydroxybenzaldehyde derivatives of the formula (I) produced by oxidation of the above-said p-cresol derivatives in accordance with the present invention are 4-hydroxybenzaldehyde, 3,5-dichloro-4-hydroxybenzaldehyde, 3-bromo-4-hydroxybenzaldehyde, 3,5-dimethyl-4-hydroxybenzaldehyde, 4-hydroxy-3-methylbenzaldehyde, 4-hydroxy-2-methylbenzaldehyde, 3,5-di-tert-butyl-4-hydroxybenzaldehyde, vanillin, 3,5-dimethoxy-4-hydroxybenzaldehyde, ethylvanillin, 3-chloro-4-hydroxybenzaldehyde, 3,5-dibromo-4-hydroxybenzaldehyde, 3-tert-butyl-4-hydroxybenzaldehyde, respectively.

The valence of the cobalt atom contained in the cobalt compound used as catalyst in this invention may be either zero-, di- or trivalent. There may be used in this invention various types of cobalt compounds, for example cobalt halide such as cobalt fluoride, cobalt chloride, cobalt bromide, cobalt iodide, etc., organic acid salts of cobalt such as cobalt acetate, cobalt octylate, cobalt stearate, cobalt oxalate, cobalt naphthenate, cobalt resinate, inorganic acid salts of cobalt such as cobalt nitrate, cobalt sulfate, cobalt borate, cobalt carbonate, cobalt cyanide, cobalt phosphate, etc., cobalt oxide such as cobalt monoxide, cobalt sesquioxide, tricobalt tetraoxide, etc., cobalt hydroxide and metallic cobalt. Cobalt complexes such as cobalt chelates are also effective as catalyst in this invention. Examples of such cobalt complexes are cobalt acetylacetonate, bis(dimethylglyoximate) cobalt porphyrin, N,N'-ethylenebis(salicylidene iminate)cobalt and N,N'-ethylenebis(3-ethoxysalicylidene iminate)cobalt. Among these cobalt compounds, hydrates or anhydrates of salts such as cobalt hydroxide, cobalt oxides, cobalt chloride, cobalt bromide, cobalt acetate, cobalt naphthenate, cobalt oxalate, cobalt sulfate, cobalt nitrate, etc., and metallic cobalt are most preferred.

The amount of the cobalt compound used is not subject to any specific restriction. Any amount not less than 0.0001 equivalent to the p-cresol derivative of the formula (II) will do, but the range of 0.0005 to 0.05 equivalents is preferred.

Any type of base having higher basicity than p-cresol derivatives of the formula (II) may be used in this invention. Examples of such bases are metal hydroxides such as sodium hydroxide, potassium hydroxide, lithium hydroxide, magnesium hydroxide, calcium hydroxide, aluminum hydroxide, etc., metal alkoxides such as sodium alkoxide, potassium alkoxide, lithium alkoxide, magnesium alkoxide, calcium alkoxide, aluminum alkoxide, etc. (the alkoxide used here may be, for example, methoxide, ethoxide, isopropoxide, tertiary butoxide, etc.), and metal amides such as lithium amide, sodium amide, potassium amide, etc. (the amide used here may be, for example, unsubstituted amide, ethylamide, diethylamide, diisopropylamide, etc.). Among the above-said bases, sodium hydroxide, potassium hydroxide, sodium methoxide, potassium methoxide, sodium ethoxide, potassium ethoxide, potassium tertiary butoxide and sodium amide are preferred.

The amount of the base used is selected without particular limitation provided that it is not less than the equivalent to the p-cresol derivative of the formula (I), but the range of 1 to 10 equivalents is preferred.

Various types of solvents, which are stable to oxygen and are capable of dissolving the starting material, may be used in the reaction of this invention. Preferred examples of such solvents are alcohols, hydrocarbons, ethers, halogenated hydrocarbons, amines, dimethylformamides, dimethylsulfoxides and the like. These solvents may be used either singly or in admixture of two or more of them. They may be diluted with water. Most preferred among these solvents are alcohols such as methanol, ethanol, isopropanol, butanol, tertiary butanol, ethylene glycol, etc.

In connection with this invention, the present inventors have found the following new facts. That is, in case of using an alcohol represented by the formula: $R_5OH$ (wherein $R_5$ is a lower alkyl group such as methyl group, ethyl group, isopropyl group or butyl group) as solvent in practicing the process of this invention, a corresponding p-alkoxymethylphenol derivative represented by the formula (III):

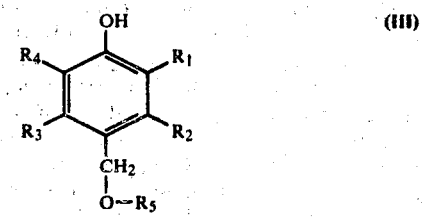

(wherein $R_1$, $R_2$, $R_3$, $R_4$ and $R_5$ are as defined above) is by-produced. It was also confirmed that the compound of the formula (III) is further oxidized under the reaction conditions of this invention to give a corresponding 4-hydroxybenzaldehyde derivative of the formula (I) which is the final product.

In the process of this invention, oxygen (oxidizing agent) may be used either singly as it is or after diluting it with a so-called inert gas (such as nitrogen or argon gas) to form an oxygen-containing gas. Air may be also used as an oxygen-containing gas.

Although no particular restriction is imposed on the pressure of oxygen or oxygen-containing gas to be used, it usually is used under a pressure between 1 and 100 atm.

The oxygen content in the oxygen-containing gas is also not subject to any specific limitation; such content may be suitably determined by taking into account such matters as safety of the operation and reaction rate.

The reaction temperature may be selected from within the range of 0° to 300° C., but the range of from room temperature to 200° C. is recommendable for assuring sufficient reaction rate.

Recovery of the starting material from the reaction mixture and isolation and purification of the object product may be accomplished by employing the commonly used methods such as concentration of the reaction mixture, acidification of the residue, extraction with an organic solvent, concentration or distillation of the extract, etc. In case the obtained 4-hydroxybenzaldehyde derivative can not be distilled, recrystallization or sublimation may be employed.

The process of this invention is described in further detail hereinbelow by way of the following examples, which are only illustrative and are not intended to limit the scope of this invention.

EXAMPLE 1

A mixture consisting of p-cresol (6.0 g, 55.6 mmol), cobalt (II) chloride (0.072 g, 0.556 mmol), sodium hydroxide (6.67 g, 168 mmol) and methanol (18 ml) was stirred in an oxygen atmosphere of 1 atm. at 60° C. for 6 hours (stirring rate: 800–1,000 rpm).

After distilling off methanol from the reaction mixture under reduced pressure, dilute hydrochloric acid was added to the residue to make it acidic and the product was extracted with ethyl acetate. The extract composition, as analyzed by gas chromatography, was as follows.

p-cresol: 0.480 g; recovery: 8%; conversion: 92%
p-methoxymethylphenol: 0.141 g; selectivity: 2%
4-hydroxybenzaldehyde: 4.86 g; selectivity: 78%

$$\text{Conversion (\%)} = \frac{\text{Moles of p-cresol consumed}}{\text{Moles of p-cresol used}} \times 100$$

$$\text{Selectivity (\%)} = \frac{\text{Moles of product}}{\text{Moles of p-cresol consumed}} \times 100$$

EXAMPLE 2

Example 1 was repeated, provided that air (freed of carbon dioxide gas and moisture) was blown into the mixture at the rate of 250 ml/min instead of using an oxygen atmosphere, and the reaction was carried out at 60° C., for 10 hours.

The reaction mixture was treated in the same way as Example 1 to obtain the following results.
p-cresol conversion: 95%
4-hydroxybenzaldehyde selectivity: 79%
4-methoxymethylphenol selectivity: 3%

EXAMPLES 3-11

Cobalt (II) chloride (0.072 g, 0.556 mmol), bases shown in Table 1 (in amounts also shown in Table 1) and solvents shown in Table 1 (in amounts also shown in Table 1) were added to p-cresol (6.0 g), and each of the obtained mixtures was vigorously stirred in an oxygen atmosphere of 1 atm. at a temperature shown in Table 1 for 6 hours. The reaction mixture was treated in the same way as Example 1, and the product was analyzed by gas chromatography. Conversion of p-cresol and selectivity of 4-hydroxybenzaldehyde (represented by A) and p-alkoxymethylphenol (represented by E; the alkoxy group is one which is derived from the alcohol used as solvent) are shown in Table 1.

TABLE 1

| Example | Base (amount used, g) | Solvent (amount used, ml) | Temp. (°C.) | Conversion (%) | Selectivity (%) A | Selectivity (%) E |
|---|---|---|---|---|---|---|
| 3 | Sodium hydroxide (4.44) | Methanol (12) | 60 | 87 | 73 | 1 |
| 4 | Sodium hydroxide (3.33) | Methanol (9) | 60 | 49 | 69 | 4 |
| 5 | Potassium hydroxide (9.33) | Methanol (18) | 60 | 92 | 76 | 2 |
| 6 | Sodium methoxide (9.00) | Methanol (18) | 60 | 90 | 68 | 10 |
| 7 | Potassium methoxide (11.7) | Methanol (18) | 60 | 92 | 75 | 5 |
| 8 | Sodium hydroxide (6.67) | Ethanol (18) | 60 | 59 | 51 | 3 |
| 9 | Potassium tertiary butoxide (18.7) | Tertiary butanol (18) | 60 | 68 | 52 | 0 |
| 10 | Sodium hydroxide (6.67) | Ethylene glycol (36) | 60 | 82 | 55 | — |
| 11 | Sodium hydroxide (6.67) | Methanol (18) | 50 | 61 | 71 | 7 |

EXAMPLES 12-21

Sodium hydroxide (7.02 g), methanol (18 ml) and cobalt compounds shown in Table 2 (in amounts also shown in Table 2) were added to p-cresol (6.0 g), and each of the obtained mixtures was stirred in an oxygen atmosphere of 1 atm. at 60° C. for a period shown in Table 2. The reaction mixture was treated in the same way as Example 1 and the product was analyzed by gas chromatography, obtaining the results shown in Table 2. Stirring was performed by using a motor in Examples 12-18 and a magnetic stirrer in Examples 19-21.

TABLE 2

| Example | Cobalt compound (Amount used mg) | Time (hr.) | Conversion (%) | Selectivity (%) A | Selectivity (%) E |
|---|---|---|---|---|---|
| 12 | Cobalt (II) chloride (36) | 6 | 92 | 75 | 2 |
| 13 | Cobalt (II) chloride (7.2) | 6 | 89 | 72 | 3 |
| 14 | Cobalt (II) acetate (98) | 6 | 93 | 75 | 4 |
| 15 | Cobalt (II) sulfate heptahydrate (156) | 6 | 90 | 71 | 6 |
| 16 | Cobalt (II) nitrate hexahydrate (162) | 6 | 91 | 70 | 3 |
| 17 | Cobalt (II) hydroxide (52) | 6 | 64 | 65 | 6 |
| 18 | Cobalt (III) hydroxide oxide (51) | 6 | 86 | 78 | 3 |
| 19 | Cobalt (II) monoxide (204) | 40 | 87 | 52 | 8 |
| 20 | Cobalt (III) sesquioxide (231) | 40 | 82 | 52 | 9 |
| 21 | Metallic cobalt (164) | 40 | 89 | 53 | 10 |

EXAMPLE 22

A mixture consisting of 2-methoxy-p-cresol (6.0 g, 43.5 mmol), cobalt (II) chloride (0.057 g, 0.435 mmol), sodium hydroxide (5.22 g, 131 mmol) and methanol (14 ml) was vigorously stirred in an oxygen atmosphere of 1 atm. at 60° C. for 6 hours. The reaction mixture was treated in the same manner as in Example 1 and the product was analyzed by gas chromatography. The starting materials were perfectly used up and formation of the following compounds was determined.
Vanillin (3.97 g; yield: 60%)
2-methoxy-4-methoxymethylphenol (0.51 g; yield: 7%)

EXAMPLES 23–33

Mixtures consisting of p-cresol derivatives (50 mmol) shown in Table 3, cobalt (II) chloride (0.5 mmol), sodium hydroxide (150 mmol) and methanol (16 ml) were vigorously stirred in an oxygen atmosphere of 1 atm. at 60° C. for the periods shown in Table 3. The respective reaction mixtures were treated in the same way as Example 1 and the products were analyzed by gas chromatography. Conversions of the respective p-cresol derivatives and selectivities of the respective 4-hydroxybenzaldehyde derivatives were as shown in Table 3.

TABLE 3

| Example | Substituents in formulae (I) and (II) $R_1$ | $R_2$ | $R_3$ | $R_4$ | Reaction time (hr.) | p-cresol derivatives of formula (II) | Conversion (%) | 4-hydroxybenzaldehyde derivatives of formula (I) | Selectivity (%) |
|---|---|---|---|---|---|---|---|---|---|
| 23 | Cl | H | H | H | 6 | 2-chloro-p-cresol | 70 | 3-chloro-4-hydroxybenzaldehyde | 63 |
| 24 | Br | H | H | H | 6 | 2-bromo-p-cresol | 65 | 3-bromo-4-hydroxybenzaldehyde | 66 |
| 25 | Me | H | H | H | 6 | 2,4-xylenol | 100 | 4-hydroxy-3-methylbenzaldehyde | 66 |
| 26 | H | Me | H | H | 6 | 3,4-xylenol | 100 | 4-hydroxy-2-methylbenzaldehyde | 62 |
| 27 | Me | H | H | Me | 4 | Mesitol | 100 | 3,5-dimethyl-4-hydroxybenzaldehyde | 59 |
| 28 | t-Bu | H | H | H | 6 | 2-tert-butyl-p-cresol | 100 | 3-tert-butyl-4-hydroxybenzaldehyde | 58 |
| 29 | t-Bu | H | H | t-Bu | 0.5 | 2,6-di-tert-butyl-p-cresol | 100 | 3,5-di-tert-butyl-4-hydroxybenzaldehyde | 52 |
| 30 | OEt | H | H | H | 6 | 2-ethoxy-p-cresol | 100 | Ethyl vanillin | 61 |
| 31 | OMe | H | H | OMe | 2 | 2,6-dimethoxy-p-cresol | 100 | 3,5-dimethoxy-4-hydroxybenzaldehyde | 55 |
| 32 | Cl | H | H | Cl | 6 | 2,6-dichloro-p-cresol | 60 | 3,5-dichloro-4-hydroxybenzaldehyde | 70 |
| 33 | Br | H | H | Br | 6 | 2,6-dibromo-p-cresol | 58 | 3,5-dibromo-4-hydroxybenzaldehyde | 68 |

EXAMPLE 34

Into a mixed cresol consisting of 30% of m-cresol and 70% of p-cresol (8.57 g, 79.4 mmol) were added cobalt (II) chloride (0.072 g, 0.556 mmol), sodium hydroxide (6.67 g, 168 mmol) and methanol (18 ml), and the resulting mixture was vigorously stirred in an oxygen atmosphere of 1 atm. at 65° C. for 5 hours.

The reaction mixture was treated in the same manner as in Example 1, and the composition of the product, as analyzed by gas chromatography, was as follows.
Recovery of m-cresol: 90%,
Conversion of p-cresol: 82%,
Selectivity of 4-hydroxybenzaldehyde: 72%,
Selectivity of 4-methoxymethylphenol: 2%.

The reaction mixture contained neither 3-hydroxybenzaldehyde nor 3-methoxymethylphenol.

Referential Example 1

Oxidation of m-cresol was carried out and the reaction mixture was treated and analyzed in the same manner as in Example 1. As a result, 99% of m-cresol was recovered, and no formation of 3-hydroxybenzaldehyde was seen.

Referential Example 2

Oxidation of o-cresol was carried out and the reaction mixture was treated and analyzed in the same manner as in Example 1. As a result, 80% of o-cresol was recovered and the production of salicylaldehyde was less than 1%.

What is claimed is:

1. A process for the production of a 4-hydroxybenzaldehyde derivative of the formula:

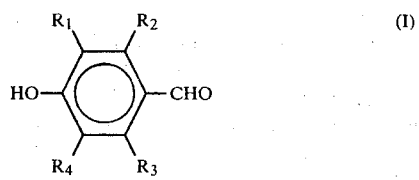

wherein each of $R_1$, $R_2$, $R_3$ and $R_4$ is selected from the group consisting of hydrogen atoms, halogen atoms, $C_1$-$C_4$ alkyl and $C_1$-$C_4$ alkoxy,
said process comprising the reaction of a p-cresol derivative of the formula:

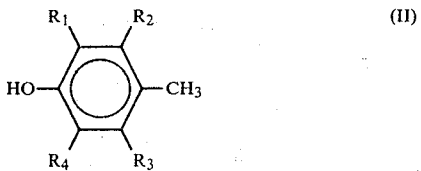

wherein each of $R_1$, $R_2$, $R_3$ and $R_4$ is as defined above, with a molecular oxygen or a molecular oxygen-containing gas in an alcohol solvent, in the presence of a base selected from the group consisting of metal hydroxides, metal alkoxides and metal amides, and a catalyst selected from the group consisting of cobalt halides, organic acid salts of cobalt, inorganic acid salts of cobalt, cobalt oxides, cobalt hydroxides, cobalt chelates and metallic cobalt, wherein the molar ratio of the base to the p-cresol derivative is in the range of 1.0–10.0 and wherein the molar ratio of the cobalt compound to the p-cresol derivative is in the range of 0.0005–0.05.

2. The process according to claim 1, in which said p-cresol derivative is p-cresol,
p-cresol,
2-bromo-p-cresol,
2-chloro-p-cresol, 2,6-dibromo-p-cresol,
2,6-dichloro-p-cresol,
2,4-xylenol,
3,4-xylenol,
mesitol,
2-t-butyl-p-cresol,
2,6-di-t-butyl-p-cresol,
2-methoxy-p-cresol,
2-ethoxy-p-cresol or
2,6-dimethoxy-p-cresol.

3. The process according to claim 1, in which said base is sodium hydroxide, potassium hydroxide, sodium methoxide, potassium methoxide, sodium ethoxide, potassium ethoxide, potassium t-butoxide or sodium amide.

4. The process according to claim 1, in which said cobalt compound is cobalt hydroxide, cobalt oxides, cobalt chloride, cobalt acetate, cobalt sulfate or cobalt nitrate.

5. The process according to claim 1, in which said solvent is methyl alcohol, ethyl alcohol, isopropyl alcohol, t-butyl alcohol or ethylene glycol.

6. The process according to claim 1, in which the reaction temperature is in the range of 20°–200° C.

7. The process according to claim 1, in which said oxygen-containing gas is air or a mixture of oxygen and nitrogen.

8. A process as claimed in claim 1, wherein said alcohol solvent is selected from the group consisting of methanol, ethanol, isopropanol, butanol, tertiary butanol and ethylene glycol.

9. A process as claimed in claim 1, wherein the reaction of said p-cresol derivative with molecular oxygen or a molecular oxygen-containing gas takes place in a reaction mixture consisting essentially of said p-cresol derivative, said molecular oxygen or molecular oxygen-containing gas, said alcohol solvent, said base and said catalyst.

* * * * *